United States Patent
Wu et al.

(10) Patent No.: US 10,238,318 B2
(45) Date of Patent: Mar. 26, 2019

(54) TREADMILL TRAINING DEVICE ADAPTED TO PROVIDE TARGETED RESISTANCE TO LEG MOVEMENT

(71) Applicant: REHABILITATION INSTITUTE OF CHICAGO, Chicago, IL (US)

(72) Inventors: Ming Wu, Wilmette, IL (US); Brian D. Schmit, Brookfield, WI (US); T. George Hornby, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 15/650,327

(22) Filed: Jul. 14, 2017

(65) Prior Publication Data
US 2017/0311848 A1 Nov. 2, 2017

Related U.S. Application Data

(62) Division of application No. 12/536,136, filed on Aug. 5, 2009, now Pat. No. 9,713,439.

(60) Provisional application No. 61/086,592, filed on Aug. 6, 2008.

(51) Int. Cl.
*A61B 5/00* (2006.01)
*A61B 5/11* (2006.01)
*A61B 5/22* (2006.01)

(52) U.S. Cl.
CPC ............... *A61B 5/11* (2013.01); *A61B 5/112* (2013.01); *A61B 5/221* (2013.01); *A61B 5/1121* (2013.01); *A61B 5/6829* (2013.01); *A61B 2505/09* (2013.01)

(58) Field of Classification Search
CPC ......... A61B 5/11; A61B 5/112; A61B 5/1121; A61B 5/1123; A63B 21/02; A63B 22/02
See application file for complete search history.

(56) References Cited

U.S. PATENT DOCUMENTS

| | | |
|---|---|---|
| 4,600,016 A | 7/1986 | Boyd et al. |
| 5,273,502 A | 12/1993 | Kelsey et al. |
| 5,314,391 A | 5/1994 | Potash et al. |
| 5,476,103 A | 12/1995 | Nahsner |
| 5,569,129 A | 10/1996 | Seif-Naraghi et al. |
| 5,885,229 A | 3/1999 | Yamato et al. |
| 5,961,541 A | 10/1999 | Ferrati |
| 5,980,435 A | 11/1999 | Joutras et al. |
| 6,063,046 A | 5/2000 | Allum |
| 6,123,649 A | 9/2000 | Lee et al. |
| 6,302,828 B1 | 10/2001 | Martin et al. |

(Continued)

OTHER PUBLICATIONS

Aoyagi et al., "Human Step Rehabilitation Using a Robot Attached to the Pelvis," Proceedings of IMECE2004, 2004 ASME International Mechanical Engineering Congress, Anaheim, California, USA, Nov. 13-19, 2014, pp. 1-6.

(Continued)

*Primary Examiner* — Max Hindenburg
(74) *Attorney, Agent, or Firm* — Drinker Biddle & Reath LLP

(57) ABSTRACT

A system and method are provided for targeted training of a person walking on a powered backward moving surface. Kinematic information of motor performance, such as ankle position and velocity, is measured throughout one or more phases of a gait cycle with a detector. The gait phase is determined, and a resistive/assistive force is applied to the leg that differs depending upon the gait phase and the measured kinematic information.

20 Claims, 12 Drawing Sheets

(56) References Cited

U.S. PATENT DOCUMENTS

| | | |
|---|---|---|
| 6,454,679 B1 | 9/2002 | Radow |
| 6,645,126 B1 | 11/2003 | Martin et al. |
| 6,666,798 B2 | 12/2003 | Borsheim |
| 6,666,831 B1 | 12/2003 | Edgerton et al. |
| 6,880,487 B2 | 4/2005 | Reinkensmeyer et al. |
| 7,125,388 B1 | 10/2006 | Reinkensmeyer et al. |
| 7,331,906 B2 | 2/2008 | He et al. |
| 7,455,620 B2 | 11/2008 | Frykman et al. |
| 7,883,450 B2 | 2/2011 | Hidler |
| 7,980,856 B2 | 7/2011 | Grabiner et al. |
| 7,998,040 B2 | 8/2011 | Kram et al. |
| 8,082,811 B2 | 12/2011 | Udono |
| 2002/0157617 A1 | 10/2002 | Reinkensmeyer et al. |
| 2004/0087418 A1 | 5/2004 | Eldridge |
| 2004/0097330 A1 | 5/2004 | Edgerton et al. |
| 2006/0052728 A1 | 3/2006 | Kerrigan et al. |
| 2006/0229167 A1 | 10/2006 | Kram et al. |

OTHER PUBLICATIONS

Colombo et al., "Treadmill training of paraplegic patients using a robotic orthosis," Journal of Rehabilitation Research and Development, vol. 37, No. 6, Nov./Dec. 2000, pp. 693-700.

Gregory et al., "Resistance training and locomotor recovery after incomplete spinal cord injury: a case series," Spinal Cord, vol. 45, 2007, pp. 522-530.

Hesse et al., "A mechanized gait trainer for restoration of gait," Journal of Rehabilitation Research and Development, vol. 37, No. 6, Nov./Dec. 2000, pp. 701-708.

Lam et al., "Contribution of Feedback and Feedforward Strategies to Locomotor Adaptations," J. Neurophysiol., vol. 95, 2005, pp. 766-773.

Riener et al., "Patient-Cooperative Strategies for Robot-Aided Treadmill Training: First Experimental Results," IEEE Transactions on Neural Systems and Rehabilitation Engineering, vol. 13, No. 3, Sep. 2005, pp. 380-394.

TREADMILL TRAINING DEVICE ADAPTED TO PROVIDE TARGETED RESISTANCE TO LEG MOVEMENT

CROSS REFERENCE TO RELATED APPLICATIONS

The present application is a divisional of U.S. patent application Ser. No. 12/536,136, filed Aug. 5, 2009, now U.S. Pat. No. 9,713,439, which claims the benefit of U.S. Provisional Application No. 61/086,592, filed Aug. 6, 2008, entitled, "TREADMILL TRAINING DEVICE ADAPTED TO PROVIDE TARGETED RESISTANCE TO LEG MOVEMENT", the entire content of all being incorporated herein by reference.

BACKGROUND

The overall goal of the invention is to enhance independent walking function in people with incomplete spinal cord injury (SCI), post stroke, and other similar injuries or conditions by minimizing the amount of walking assistance provided or by adding targeted resistance to the legs during body weight supported treadmill training (BWSTT). Providing targeted resistance load based on the motor performance of the patient improves the training outcomes of BWSTT through enhanced patient effort that effectively engages adaptive sensorimotor processes.

Spinal Cord Injury

The estimated prevalence of SCI in the United State is approximately 253,000 individuals. Approximately 52% of the people with SCI suffer from functionally incomplete spinal cord injury and could benefit from gait retraining. With the emergence of new treatments such as cell implants, the use of growth-stimulating factors and other technologies, the number of people with SCI needing gait retraining is likely to increase even further.

One of the most common goals of patients with SCI is regaining walking ability, as limitations in mobility can affect most activities of daily living. Following an SCI, descending spinal pathways are damaged. The loss of descending input to spinal neurons may reduce synaptic drive to locomotor networks and also compromise the ability to produce voluntary movements of the limbs. As a result, an obvious consequence of SCI is paralysis, or weakness of lower extremity muscles that may have a substantial adverse impact on walking.

Individuals with SCI may suffer difficulties supporting their body weight during the stance phase of gait or lifting and bringing the leg forward during swing due to the muscular weakness associated with the injury. As a consequence, people with SCI often require assistive devices, such as a rolling walker, and spend more of the gait cycle in double support (i.e., bearing weight in both legs to improve support).

In general, successful locomotor recovery following SCI depends on the availability of residual descending commands and on maximizing neural plasticity of spinal and supraspinal locomotor networks. The neural reorganization achieved during rehabilitation is highly dependent on the magnitude and specificity of targeted neural activity. Thus, to maximize motor recovery, the various embodiments of the present invention offer rehabilitation after neurological injury that emphasizes active, repetitive, task-specific practice that maximizes neuromuscular activity.

Current BWSTT techniques are generally designed to improve motor function and ambulation in people with SCI. During such current BWSTT, the patient is given body weight support and assisted to move their legs in a "kinematically correct gait" by a physical therapist. This training paradigm largely meets criteria for effective neuroplasticity: the training is task-specific and utilizes both active and sensory pathways of the relevant neuromuscular systems.

Stroke

Stroke is currently the leading cause of disability in the U.S. with approximately 1.1 million individuals currently with stroke-related disabilities. Impaired mobility is an important factor in determining the degree of physical disability after stroke. While up to 80% of individuals with stroke may ultimately recover the ability to walk short distance, most of them do not achieve the locomotor capacity necessary for community ambulation. Walking ability post-stroke is characterized primarily by reduced walking speed and endurance, residual spatial and temporal left-right asymmetry, and impaired postural stability. Patients post-stroke suffer a greatly reduced knee flexion at toe off and peak knee flexion during swing of the paralyzed leg compared to the intact leg, which is usually associated with compensation by pelvic hiking and limb circumduction. The impaired hip and knee flexion during swing phase may result in a decreased forward progression and velocity, shortened step length and toe drag at initial swing. These impairments restrict independent mobility and severely impact post-stroke patients' quality of life.

Decreased overground walking speed is a result of decreased cadence, decreased stride length and increased non-paretic single limb stance duration. Mechanisms underlying reduced gait velocity are thought to be the weakness of the paretic limb, particularly hip flexor and plantarflexor strength, spasticity, and the loss of inter- and intra-limb coordination. Rehabilitation efforts to improve strength and muscle coordination patterns during hemiparetic gait may improve gait velocity and quality and therefore improve performance of activities of daily living.

To improve gait performance and functional outcomes following neurological injury, rehabilitation efforts have been focused on re-establishing normal walking patterns. Towards this end, the use of BWSTT has demonstrated significant improvement in walking capability in individuals post-stroke. By providing a portion of body weight over a treadmill and manual facilitation from therapists, research has demonstrated improvements in temporal-spatial gait patterns, including gait velocity, endurance, balance, and symmetry.

While statistically significant improvements in walking recovery with BWSTT have been shown, it remains unclear whether therapeutic effects of such training are maximized. Specifically, in studies that have employed high intensity walking regimens in individuals with chronic stroke (i.e., those without presumed spontaneous recovery), the average increase in walking speed ranges have been achieved. These increases equating to an increase of approximately 10% of healthy adult walking speed are small relative to the effort required to perform such training. In addition, the major limitation of BWSTT is that it requires greater involvement of the physical therapist, i.e., generally two or even more therapists are required in setting the paretic limb and controlling the trunk movement, and it is a labor intensive work for physical therapists, particularly for those patients who require substantial walking assistance following stroke. As a consequence, there is a need to produce greater functional improvements in a larger patient population.

Current Robotic Systems

Due to these limitations in BWSTT, several robotic systems have been developed for automating locomotor training, such as the Lokomat gait trainer (Colombo et al. "Treadmill Training of Paraplegic Patients Using a Robotic Orthosis," *J. Rehabil Res. Dev.* 37:693-700 (2000)) and the Gait Trainer (GT) (Hesse et al. "A Mechanized Gait Trainer for Restoration of Gait," *J. Rehabil Res. Dev.* 37:701-708 (2000)). The Lokomat gait trainer is a motorized exoskeleton that drives hip and knee motion with a fixed trajectory using four DC motors, but it is difficult to back drive the Lokomat because it uses high-advantage, ball screw actuators. The Gait Trainers rigidly drive the patient's feet through a stepping motion using a crank-and-rocker mechanism attached to foot platforms. These robotic systems had at their onset the basic design goal of firmly assisting patients in producing correctly shaped and timed locomotor movements.

This approach is effective in reducing therapist labor in locomotor training and increasing the total duration of training but shows relatively limited functional gains for some patients. For instance, in tests, only 0.06 m/s gait speed improvement was obtained following 4 weeks of training using a Lokomat. Especially, recent data indicate that robotic-assisted BWSTT is even less effective in improving walking ability in individuals post stroke than physical therapist-assisted locomotor training. Such results suggest that currently available robotic-assisted BWSTT does not significantly help stroke patients or individuals with SCI regain gait function so that their principal benefit is in reducing the labor effort of the physical therapist.

The limited effectiveness of current robotic systems for locomotor training may be due to the employment of the fixed trajectory control strategy. The algorithms that have been used in current available robotic systems for locomotor training have focused primarily on repeated movements of the limbs via predefined, fixed-kinematic trajectories, although new control algorithms have been tested recently (Riener et al. "Patient—Cooperative Strategies for Robot-Aided Treadmill Training: First Experimental Results," *IEEE Trans Neural Syst. Rehabil. Eng.*, 13:380-94 (2005)).

This type of training, however, eliminates cycle-to-cycle variation in the kinematics of the leg, a fundamental feature of the natural neural control of repetitive movements such as stepping. Indeed, fixed kinematic trajectory may lead to a learned helplessness condition, in which patients have less self-controlled success in generating the appropriate stepping movement of the lower limbs. In addition, a robotic orthosis driven in a fixed pattern effectively limits the degrees of freedom of the leg motion as compared with naturally occurring muscle activation patterns.

In contrast, the present inventors have determined that motor learning is more effective with a robotic algorithm that allows some variability in the stepping pattern than with a fixed trajectory paradigm. Thus, a training algorithm that permits the intrinsic variability in the activation of motor pools may allow the spinal circuits to explore multiple patterns of activation and thereby optimize training effectiveness. Thus, the system of the present invention does not precisely control the trajectory of the leg, but rather allows patients freedom to volitionally move their legs during treadmill walking using a novel cable robotic system.

The resulting variations from step to step are believed to be an important feature in motor learning in accordance with the present invention. There are many examples of tasks having some intrinsic level of variation in both the biomechanics and the timing of the neurons recorded during the repetitive performance of the task. Stepping is an excellent example of a motor task that is performed routinely and repetitively, but even under the most controlled conditions on a treadmill, no two steps are identical. This intrinsic variation in stepping is highly suggestive of a fundamental feature of the neural control of movement. It is already known that complete and stereologically constant assistance reduces the level of activation of the motor circuits that generate stepping. Thus, the system does not control the kinematics of the lower limbs during stepping in a manner that produces minimal variation—a minimal variation results in poorer stepping ability than if some level of variation is allowed during the stepping.

Rather, variation in stepping can be retained during treadmill stepping by applying assistance as needed (AAN). An experienced therapist may guide the patient to achieve a targeted motion trajectory, giving help only when the patient exhibits a large deviation from some desired trajectory or has difficulty in performing the movement. By applying AAN, the efficacy of BWSTT is improved by increasing patient effort and active involvement in motor learning.

This is supported by observations that active motor training is more effective than passive training in eliciting performance improvement. Evidence from spinalized mice indicates that motor learning is more effective with AAN than with a fixed trajectory paradigm. In addition, therapist-assisted treadmill training using an AAN strategy facilitates greater improvements in walking ability in ambulatory stroke survivors as compared to robotic-assisted training using a fixed trajectory paradigm. Thus, applying a controlled load using an AAN strategy encourages the active involvement of the patient to enhance the training efficacy of robotic BWSTT.

For high functioning patients, an assistance only training paradigm may be less effective than no assistance for improving walking ability. Thus, the present system applies an adaptive disturbance load to the paretic leg of ambulatory stroke patients to produce a deviation in step kinematics, thereby improving the efficacy of BWSTT. This is supported by results from arm training in patients post stroke. Specifically, data from hemiparetic subjects practicing upper limb movements with forces that provide passive guidance vs. error enhancement indicate that greater improvements in performance are achieved when errors are magnified. These results indicate that causing adaptation by using error-augmentation training might be an effective way to promote functional motor recovery for patients with stroke.

In addition, results from locomotor training in healthy subjects show that motor learning is accelerated by amplifying, rather than reducing, movement errors. Thus, applying a tolerated disturbance load to produce kinematic deviations of the leg during treadmill training may accelerate the motor learning during BWSTT in the patient following a stroke or spinal cord injury.

Motor adaptations driven by disturbance loading may produce 'aftereffects' that improve stepping performance and eventually enhance training paradigms. In animal preparations, locomotor behavior can be conditioned to overcome an obstacle and the animal continues to step with an elevated trajectory on the removal of the obstacle. This aftereffect suggests a remodeling of locomotor patterns in anticipation of the perturbation. There is similar evidence from human experiments showing lasting modifications in response to sustained alterations in walking conditions. Human infants and adult subjects adapt to the constant presence of a disturbance to swing phase movements and show aftereffects upon removal of the disturbance.

There is also evidence for modifications in interlimb coordination after a period of walking on a rotating disk or a split-belt treadmill. The presence of aftereffects after a period of training with a disturbance implies the formation or recalibration of the motor output for a given task, suggesting that adaptive training might also prove useful during gait rehabilitation. It is likely that these motor adaptation mechanisms are driven by kinematic deviations from a normal walking pattern, such that disturbances to the leg during stepping can be used to increase the drive to the leg through a motor adaptation mechanism. These motor adaptations, which occur relatively rapidly, are likely to engage neural pathways useful for enhancing longer-term (weeks) training. A durable long-term adaptation may be a consequence of repeated exposures to rapid short-term plasticity associated with a given dose of training.

SUMMARY

While BWSTT techniques have been shown to provide improvements in locomotor ability, motor function and balance, an objective of various embodiments of the present invention is to improve the efficacy of the technique by minimizing the amount of assistance provided, and allowing independent walking practice. Thus, as described below, the invention provides minimal assistance, or even tolerated resistance to movement during targeted phases of gait to enhance the training effects of BWSTT.

Various embodiments of the present invention can also make BWSTT better for SCI patients through increased patient effort (i.e., enhancing descending drive) and/or by engaging adaptive sensorimotor processes that are sensitive to errors in trajectory. The design also has potential for long term transfer to overground gait following repeated exposures.

Another goal is to improve the efficacy of BWSTT in people post stroke using a novel robotic therapy that applies forces to the paralyzed leg during the swing phase of gait. Similar to treatment of SCI patients, a controlled load is applied to the paralyzed leg at the ankle starting from late stance to mid swing through a novel, cable-driven actuator while subjects walk on a treadmill. Providing assistance as needed (AAN) or resistance as tolerated (RAT), using a load based on the motor performance of the patient improves the training outcomes of BWSTT through enhanced patient effort that effectively engages adaptive sensorimotor processes.

In assessing the motor adaptation to a disturbance (resistance) load in individuals with, e.g., chronic (>6 month) stroke (or SCI>12 month) in accordance with various embodiments of the invention, a controlled resistance load is applied to the paralyzed leg at the ankle, thigh, or other location during the early swing phase of gait (which is between a toe-off and heel-contact part of the gait) through a cable robot, while the subjects walk on a treadmill. The load is controlled and automatically real-time adjusted based on kinematic performance to maintain a stable stepping.

Partial body weight support may be provided to assure a stable stepping pattern on the treadmill while the treadmill speed is preferably set at the maximum comfortable speed. The electromyography (EMG) from eight muscles (tibialis anterior, soleus, medial gastrocnemius, vastus medialis, rectus femoris, vastus lateralis, lateral hamstrings and medial hamstrings) of each leg and the kinematics of the lower extremities may be recorded to quantify the motor adaptive effects of the applied loads. Silver/silver chloride electrodes may be applied to lightly abraded skin over the belly of each muscle, and shielded leads will be attached to a preamplifier/filter system (amplification 1000×, band-pass filter at 20-400 Hz). All signals should be electrically isolated, amplified, filtered (400 Hz low pass) and sampled at 500 Hz using a data acquisition board (National Instruments) on a PC with custom LabVIEW (National Instruments, Austin, Tex.) software.

Leg muscle activity and limb kinematics adapt to the applied loads and show aftereffects when removed. Specifically, enhanced flexor muscle activities are produced in the lower limbs during adaptation to the targeted perturbation and enhanced kinematics, such as increased step height and stride length, following the removal of disturbance load. Further, the enhanced kinematics carry over to overground walking. Locomotor recovery may be assessed using a resistance as tolerated/assistance as needed strategy to control the load applied to the paralyzed leg during BWSTT.

Using the resistance as tolerated/assistance as needed strategy improves BWSTT in patients post stroke (and in patients with SCI). In addition, the control algorithm optimizes the amount of the applied load based on the ongoing motor performance of the patient during training, thereby improving gait in individuals post stroke or with SCI through robotic-assisted BWSTT.

While in most cases motor adaptation and associated aftereffects are short-lived, the phenomenon has the potential for clinically significant changes following repeated exposure. While limited studies have demonstrated a long term (weeks) retention of motor adaptation using repeated measures, results from the use of the present system indicate a significant cumulative effect consisting of the increased gait speed and step length of the paralyzed leg following repeated exposure to resistance load training after two weeks training for six sessions. Thus, the motor adaptation to disturbance load and the after-effects can be utilized to improve the motor performance of gait following the repeated exposure of the intervention in individuals post-stroke.

According to various embodiments of the invention, walking function is enhanced in people with incomplete SCI or post stroke by adding targeted resistance in order to increase patient effort and augment motor adaptation. Targeted resistance improves BWSTT through increased patient effort and by engaging adaptive sensorimotor processes, especially for higher-functioning patients. In addition, using an AAN/RAT strategy in robotic locomotor training significantly increases the efficiency of robotic treadmill training. Various embodiments of the present invention provide a targeted resistance load as tolerated instead of persistent assistance to increase patient effort and further improve the efficacy of BWSTT by engaging adaptive sensorimotor process. Finally, the use of an AAN/RAT strategy in robotic locomotor training improves functional outcomes in patients with incomplete SCI or post stroke to a greater extent than previously-used assistance training paradigms.

One feature of this new system is that the trajectory of the gait pattern is not fixed as it is for a crank-and-rocker mechanism, as used in Gait Trainer (Hesse and Uhlenbrock 2000), but is flexible to allow patients to produce a natural dynamic stepping trajectory. Thus, the present system does not precisely control the trajectory of the leg, but rather, controls the load applied to the leg during treadmill walking using a novel cable robotic system.

In addition, it is highly back-drivable, i.e., a human subject can perform a user-driven movement in the workspace with minimal opposition. The high backdrivability of the current system may be achieved by using motor directly driven cable spool and a light weight cable driven to apply controlled force to the leg (rather than a controlled trajectory). This feature has advantages over the ball-screw mechanisms used for the Lokomat (Colombo et al. 2000), allowing patients to make and correct errors across steps. The current system is highly backdrivable, compliant and allows freedom for patients to voluntarily move their legs during BWSTT.

Accordingly a system is described herein for providing targeted training to a walking person, comprising: a powered backward moving surface that the person walks on; a force-applying element affixed to a leg of the person; a gait phase detector; at least one of a leg portion position sensor and a leg portion velocity sensor; a motor connected to the force-applying element; and a controller comprising: an input connected to the gait phase detector; an input connected to the leg portion position or leg portion velocity sensor; an output connected to the motor; and an algorithm that accepts values related to a gate phase from the gait phase detector, to the leg portion position or leg portion velocity and outputs a value related to a resistive force of the motor applied to the force-applying element based on the gait phase.

An associated method is described for providing targeted training to a person walking on a powered backward moving surface, comprising: measuring kinematic information of motor performance of a leg of the person throughout one or more phases of a gait cycle with a detector; determining a phase of the gait; and applying a resistive force to the leg that differs depending upon the gait phase. A computer program product is also provided, comprising a computer usable medium having a computer readable program code embodied therein, the computer readable program code adapted to be executed to implement the method.

DESCRIPTION OF THE DRAWINGS

The invention is described below with reference to various embodiments illustrated in the drawings and following description.

DETAILED DESCRIPTION OF THE EMBODIMENTS

Physical System

Figure 1A:
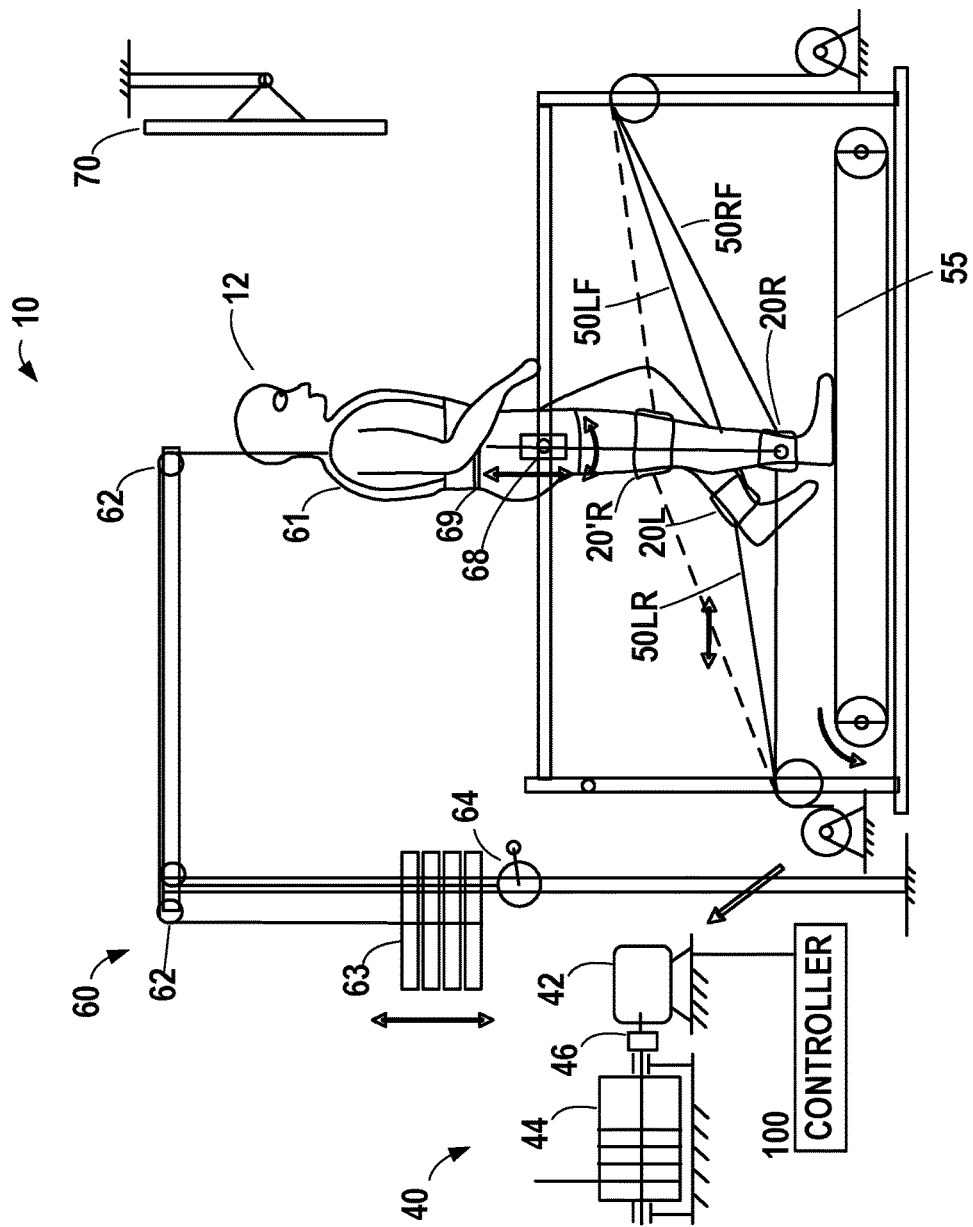
FIG. 1A is a pictorial diagram of an embodiment of the treadmill training device.

The novel cable driven system/robot 10, according to an embodiment of the invention as illustrated in FIG. 1A, has been developed to aid a person 12 undergoing therapy to provide assistance/resistance load to the person's legs at the ankle or above the knee during locomotor training.

Assistance or resistance of an amount calculated by a computer algorithm in a controller is provided to the legs of a person walking on a powered backward moving surface, such as a treadmill, at a specific phase of the gait cycle in order to maintain a stable stepping. In order to encourage an active training, and given exhaustion by the person, the load must be varied over time.

As can be seen in the embodiment illustrated in FIG. 1A, holding elements, such as custom braces 20R, 20L (R and L designating right and left—collectively element 20) or other holding elements are preferably strapped to a lower thigh region or ankle of the person 12 to provide resistance or assistance load during the swing phase of locomotion, although other leg attachment points (shin, upper thigh) could potentially be used as well.

The braces 20 are connected to a drive system 40 via connecting elements 50RF, 50RR, 50LF, 50LR (R and L designating right and left, F and R designating front and rear—collectively element 50) serving as force-applying elements that, in a preferred embodiment, comprise four nylon-coated stainless-steel cables (1.6 mm diameter), driven by four motors 42RF, 42RR, 42LF, 42LR (collectively element 42) (AKM33H, Kollmorgen, Drive amplifier, Servostar 30661) through four cable spools 44RF, 44RR, 44LF, 44LR (collectively element 44) and pulleys 45RF, 45RR, 45LF, 45LR (collectively element 45), the cables 50 being affixed to custom braces 20. Other types of movement actuators, including rigid members such as bars, could also be used—and in this case, only one per brace need be used. One spool per cable as a part of the movement actuator is provided in the preferred embodiment, although an alternate design is to have both a front and rear cable for a given leg brace to be wound on the same spool, in opposite directions so that an extension of one (e.g., front) cable corresponds with a retraction of the other (e.g., rear) cable.

Four one-degree-of-freedom reaction torque load cells 46RF, 46RR, 46LF, 46LR (collectively element 46) (TRT-200, Transducer Techniques, Temecula, Calif.) may be integrated between the output shafts of the motors 42 and the cable spools 44 to record applied torques, although other mechanisms for measuring applied force could be used. A pretension force of 2-3N may be applied to both the forward and reverse cables to prevent slack, assuring the other leg does not get snagged. A monitor 70 may be set in front of the person 12 to provide visual feedback of his/her motor performance.

The operator can control the cable robot 10 at a high level via a user interface that may be programmed in, e.g., LabVIEW (National Instruments, Austin, Tex.), with personal safety ensured by a mechanical stop, an accessible panic switch, and monitoring by a licensed physical therapist with knowledge of the cable robot 10 at all times during gait training. Side support may be provided using a group of springs 68 attached to a torso harness 69 at the level of the pelvis.

The ankle trajectory signals may be measured using, e.g., a custom designed 3-dimensional position detector. This comprises a detector bar and two joints located at the two ends of the bar. At the lower end of bar, it has a U-joint with 2 rotational degree of freedom (DOF) through which the bar is attached to the ankle with a strap. At the upper end of the bar, it has a U-joint with 3 DOFs (1 linear and 2 rotational) through which the bar is attached to the frame located at the side of the treadmill. The rotation center of the U-joint at the upper end may be adjusted to align with the hip joint to estimate the hip joint angle. Two potentiometers (P2201, Novotechnik, Southborough, Mass.) may be used to measure the rotational angular position and 1 linear position transducer (SP-2, Celesco, Chatsworth, Calif.) may be used to measure the linear position of the bar. Other mechanisms, such as imaging systems, accelerometers, and the like could also be used as well. It is also possible to measure any one of position, velocity, acceleration, and calculate the others from the measured values.

The horizontal position and velocity signals of the ankle may be used by the operator to control the timing of loading and unloading, and to determine a specific load amount to apply at each step. The horizontal velocity of the ankle may be used as a trigger to start loading from the late stance to mid swing. The amount of the load will be real-time calculated by comparing the difference between the normalized ankle horizontal position and velocity and the measured values. The position and velocity gains may be determined at the beginning of the training and depend on the tolerance of each subject.

Although other delineations of gait phase may be utilized, the gait phases can generally be broken down into a post-heel-contact phase, a pre-toe-off phase, a post-toe-off phase, and a pre-heel-contact phase.

Subjects may utilize a counterbalancing system 60 and be fitted with an overhead harness 61 attached to a pulley 62/counterweight 63 support system. The counterweight 63 can be adjusted, e.g., via a winch 64 to support from 0 to 100% of the person's 12 body weight during treadmill stepping. The person 12 should wear comfortable shoes and walk on a treadmill 55 (Woodway, Waukesha, Wis.) at their maximum comfortable velocity.

In sum, as illustrated in FIG. 1A, the motor driven cable apparatus with body weight support system 10 comprises four cables 50 driven by four motors 42, pulleys, and cable spools 42 are used to apply resistance/assistance load during the swing phase of walking. A personal computer, as a controller 100, may comprise algorithms that accept information provided to the computer related to the motor performance of the person as they are walking on the treadmill, and calculate an amount of force that is to be applied to the legs of the person.

Controller

Figure 1B:
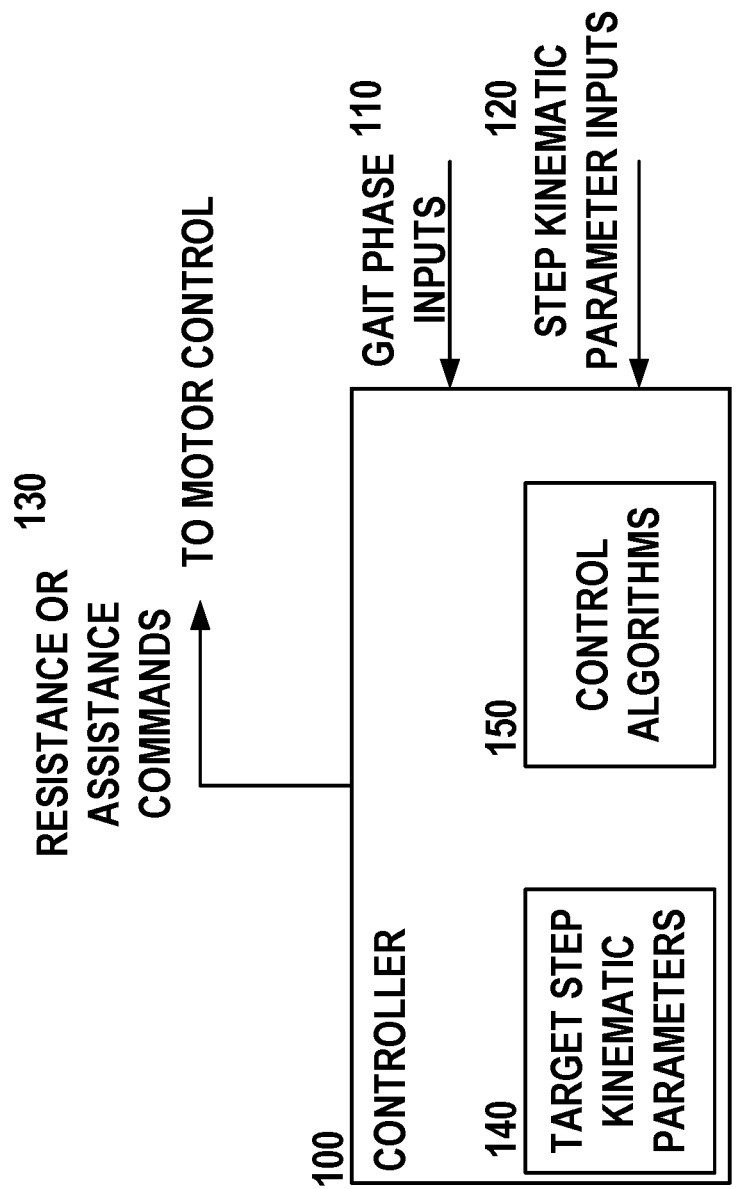
FIG. 1B is a block diagram of an embodiment of the controller.

As illustrated in FIG. 1B, the controller 100 is designed to automatically adjust the amount of assistance or resistance provided by the cable robot 10 based on the motor performance of the person 12. The adaptive control algorithm uses an assistance as needed/resistance as tolerated (AAN/RAT) strategy. For example, to determine the appropriate amount of resistance to forward motion of the leg during a phase of the gait, which is determined by gait phase inputs 110, it is desirable to resist the leg movement without dramatically disrupting the overall kinematic pattern of walking. Toward this end, motor performance for this task is quantified using kinematic information from the legs 120, and resistance or assistance commands 130 are provided to the motor control as determined.

The controller automatically adjusts the load provided by the cables, based on the kinematic performance of the subject. The control algorithm can be designed for an assistance or resistance strategy. The load may be applied starting at pre-swing (10% gait cycle prior to toe off) through mid-swing of gait on the paretic leg. For the assistance paradigm, the assistance force provided is proportional to the kinematic error during the swing phase. Specifically, the force applied to the legs is determined using the following equation:

$$F_a(t) = -k_P(x(t)-x_d(t)) - k_D(\dot{x}(t)-\dot{x}_d(t)) \tag{1}$$

where

T is time;

$F_a(t)$ is the applied assistive force as a function of time;

$k_P$ is a subject- and session-specific position gain; its value is determined at the beginning of each training session and depends on the tolerance of each subject. A larger value of $k_P$ represents a larger force to be applied to the leg for a given ankle position error, i.e., the difference between the measured position value and normalized value obtained from healthy subject;

$k_D$ is a subject- and session-specific velocity gain; the value is determined at the beginning of each training session. A larger value of $k_D$ represents a larger force to be applied to the leg for a given ankle velocity error, i.e., the difference between the measured ankle velocity and normalized values obtained from healthy subject;

$x(t)$ is the measured ankle horizontal position during the swing phase;

$\dot{x}(t)$ is the measured ankle horizontal velocity during the swing phase;

$x_d(t)$ is the desired ankle horizontal position during the swing phase; and $\dot{x}_d(t)$ is the desired ankle horizontal velocity during the swing phase;

The desired positions and velocities are determined from the mean recorded the ankle trajectory using the position sensor for two healthy subjects walking on the treadmill. These position and velocity signals are then normalized via interpolation using a cubic spline to the mean step duration.

Figure 3:
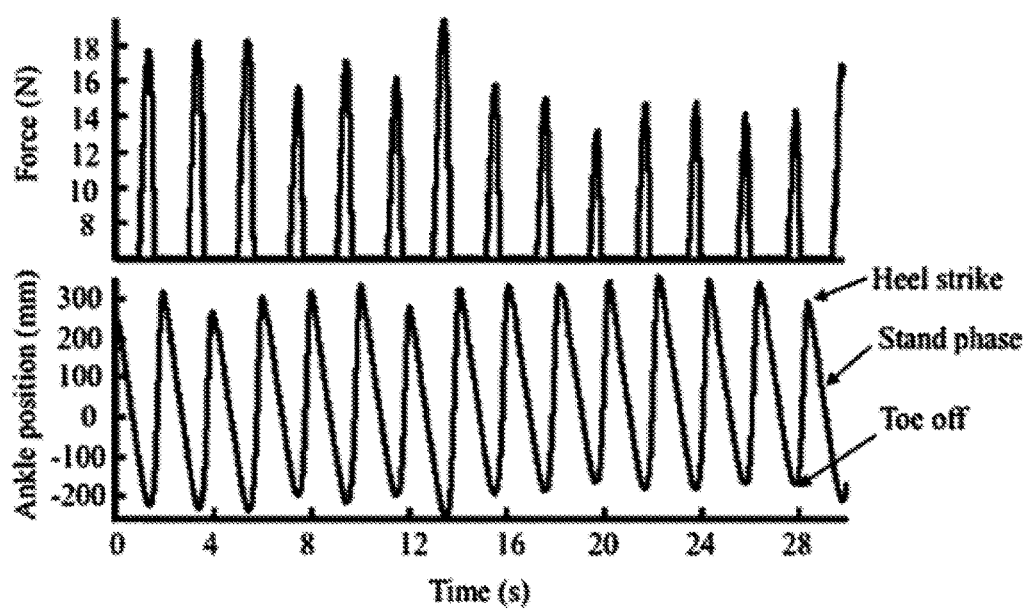
FIG. 3 is a graph showing an exemplary assistance force applied to the leg of one subject post stroke during treadmill training.

The assistance force applied to the leg of one subject post stroke during treadmill training is shown in FIG. 3.

This Figure shows the assistance force produced by the cable robot and ankle horizontal position of one subject following chronic stroke (female, left-side paretic weakness, 38 years old and 28 months post stroke) during treadmill walking. The subject walked on a treadmill with their maximal comfort speed, set at 1.7 kmph. No body weight supported was provided but a harness was used for safety only.

Figure 1C:
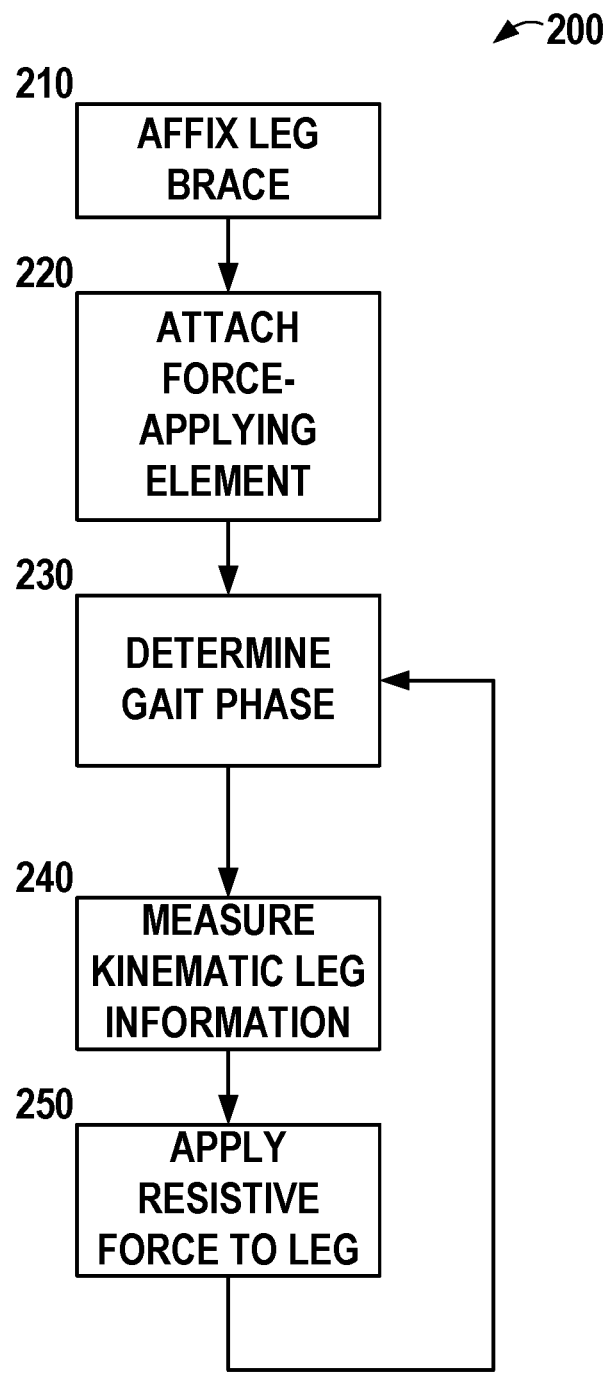
FIG. 1C is a flowchart illustrating basic steps in an exemplary method embodiment.

For the condition with resistance training, it is desirable to resist the leg without dramatically disrupting the overall kinematic pattern of walking. Toward this end, the controller is designed to provide a resistance force such that if the kinematic error is too large, the resistance force decreases. However, if the kinematic error is small (more close to the normal pattern), the resistance force increases to maintain some level of error. Specifically, the resistance force applied to the leg is determined using the following equation:

$$F_r(t) = k_P(e_t - (x_d(t) - x(t))) + k_D(\dot{e}_t - (\dot{x}_d(t) - \dot{x}(t))) \quad (2)$$

where
$e_t$ is the preset threshold value for the position errors: $e_t$=280 mm nominal; and
$\dot{e}_r$ is the preset threshold value for the velocity errors: $e_t$=25 mm/s nominal.
$F_r(t)$ is the applied resistive force as a function of time;

FIG. 1C is a basic flow chart 200 highlighting the primary process steps. A leg brace is affixed to the leg at some position 210, preferably the ankle or lower thigh. A force-applying element is attached to the leg brace 220, which could include a bar, cable, or any other connecting element capable of providing a moving force to the brace. A gait phase is determined 230, and at the proper gait phase, a force is applied.

In addition, a monitor 70 may be set in front of the person 12 to provide visual feedback about motor performance using, e.g., two bars with different color and height, and the ankle trajectory. Specifically, two bar graphs can be displayed on the screen to indicate the kinematic performance of two legs. This feedback as an adjunct to provide the motivation to the person 12 for further improving their performance throughout the course of the training.

Studies and Results

Study 1

To assess the impact of targeted resistance load on the locomotion in individuals with SCI, one subject with incomplete spinal cord injury (Male, 45 years old, injury level at C5, the time post injury was 37 months and American Spinal Cord Association (ASIA) classification D) was invited to participate in a pilot study. The patient's scores on the Walking Index for Spinal Cord Injury II (WISCI II) was 16/20. The score on the Lower-Extremity Motor Score (LEMS) was 50/50, and the 10-Meter walking speed was 0.51 m/s. The subject was fitted into an overhead body weight support system through a harness (for safety only and no body weight was supported) and walked on a treadmill with the speed set at 1.8 kmph. A cable was attached to the right leg at the ankle using a strap, which was then connected to the cable spool to provide a constant resistance (backward) or assistance (forward) load to the lower leg. The loads applied to the legs were controlled through a PC using custom Lab VIEW software.

Two types of loads, resistance and assistance, were applied to the right leg through the cable, with a 10 minute interval between the application of the loads to allow washout of any lingering aftereffects. A constant load, 5 N for the first 20 steps, 15 N afterwards, was applied to the ankle through the cable-driven system according to an embodiment of the invention for the purpose of the pilot test. For each test run, the subject walked on the treadmill without load for 2 minutes, defined as the baseline period, and then a resistance or assistance load was applied to the leg for 5 minutes, defined as the adaptation period, and after that, the load was removed and the subject continued to walk on the treadmill for another 1 minute, defined as the post-adaptation period.

Surface EMG data from 6 muscles of the right leg were recorded using active Delsys electrodes (model De 2.1, Delsys Inc., Boston, Mass.). Kinematic data from the hip, knee and ankle were recorded using three electrogoniometers (Biometrics, Inc, UK) attached at the hip, knee and ankle. The length of the lower leg, measured between the ankle and knee axes of rotation and the length of the femur were measured for subsequent calculations of the step height and stride length. All data were sampled at 1000 Hz using a data acquisition card (National Instruments, Austin, Tex.). Data were recorded starting from 1 minute prior to the load application to 1 minute after the load was released. After 10 minutes rest, the test run was repeated using assistance load. The step height and stride length were calculated using the hip and knee joint angle signals and the length of lower limb.

The load resistance and assistance tests appeared to have different effects on gait kinematics, measured using step height and stride length of the right leg. Providing resistance during the swing phase of gait enhanced the training effects through increased patient effort, and an aftereffect consisting of increased step height and stride length following the load release was observed, as shown at FIG. 2B.

Figure 2:
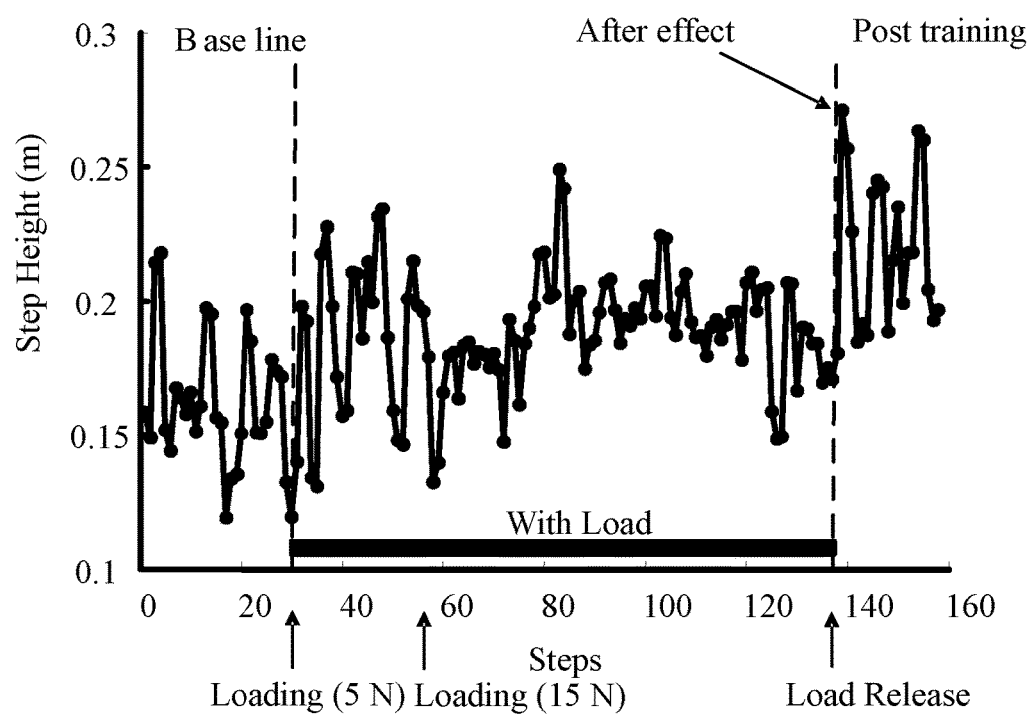
FIG. 2 is a graph showing a kinematic measure of the person's leg after the resistance treatment.

Interestingly, the subject even overcompensated for the resistance load during the initial loading period (see FIG. 2B). To identify the training effect of resistance loads, the average step height and stride length during the baseline (3 strides right before loading), and the 3 strides following load release were calculated. Following 5 minutes of resistance training, both the step height and stride length were increased with a more significant increase for step height (see FIGS. 4A and 4B). In addition, the feedback from the subject was extremely positive. He felt his trained leg (right leg) was much lighter following the resistance load training and wanted to participate in a future training protocol.

Thus, FIG. 2B is a graph showing a stride by stride plot of step height for one subject with incomplete SCI. A constant resistance load was applied to the ankle through a custom strap using the cable driven system 10. As a safety precaution, 5N load was applied first and then the load was increased to 15N. The resistance load was released following 5 minutes training on the treadmill.

Figures 4A, 4B:
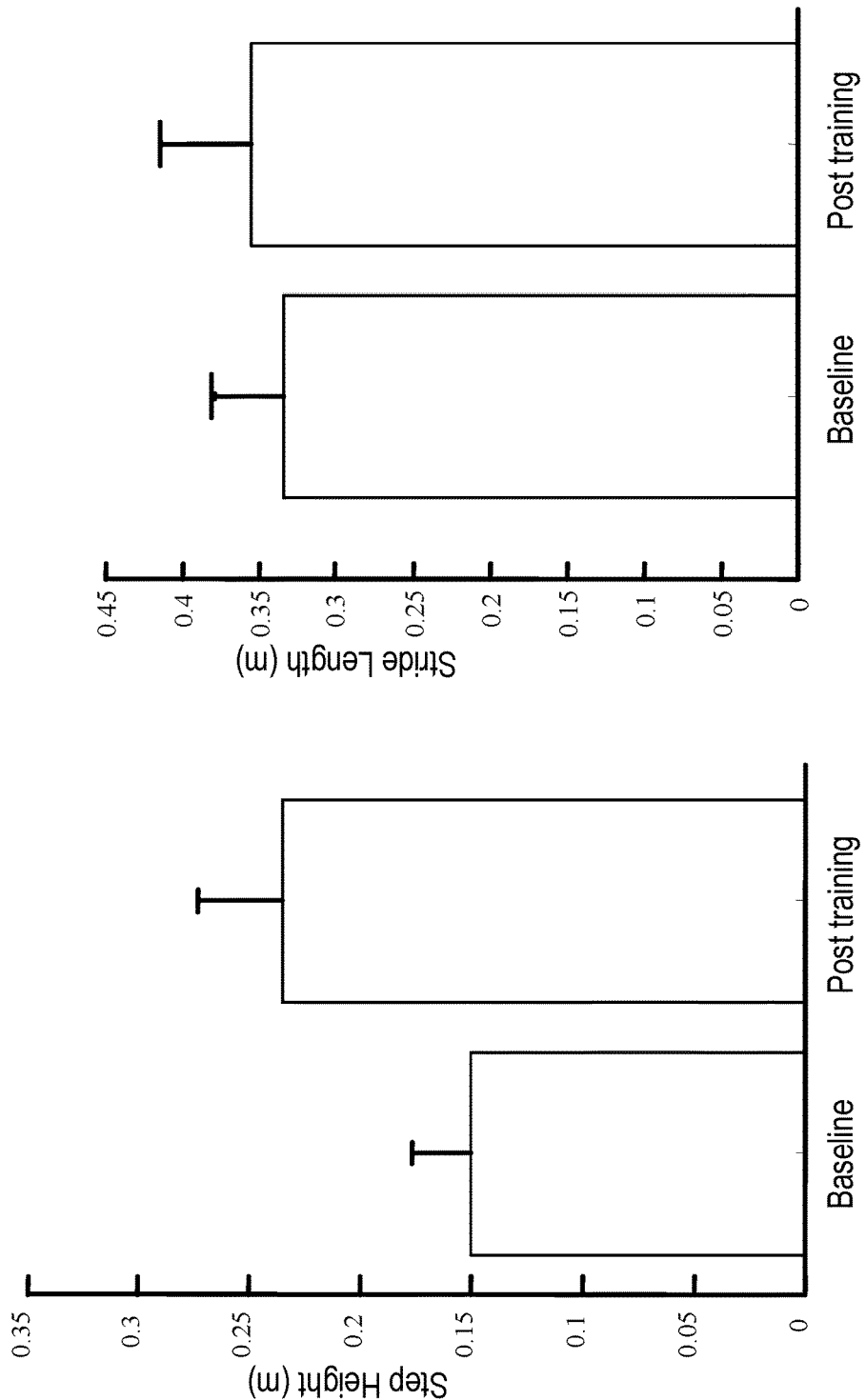
FIG. 4A is a graph showing the average step height of three strides at the baseline (before loading) and post load release for resistance load training.
FIG. 4B is a graph showing the average stride length of three strides at the baseline (before loading) and post load release for resistance load training.

FIGS. 4A and 4B are graphs showing the average step height, (FIG. 4A), and stride length, (FIG. 4B), of three strides at the baseline (before loading) and post load release for resistance load training. A constant resistance load (15N) was applied at the ankle through the cable driven system during the swing phase of the gait. The error bar indicates the standard deviation of the step height and stride length of three strides.

In contrast, persistent assistance load applied to the ankle appeared to reduce the patient effort during treadmill stepping. Following 5 minutes walking with constant assistance (15N), the patient adapted to this assistance perturbation, and demonstrated an aftereffect following the load release. In order to identify the training effect of assistance loads, we calculated the average step height and stride length during the baseline (3 strides before loading), and the 3 strides following load release.

Figures 5A, 5B:
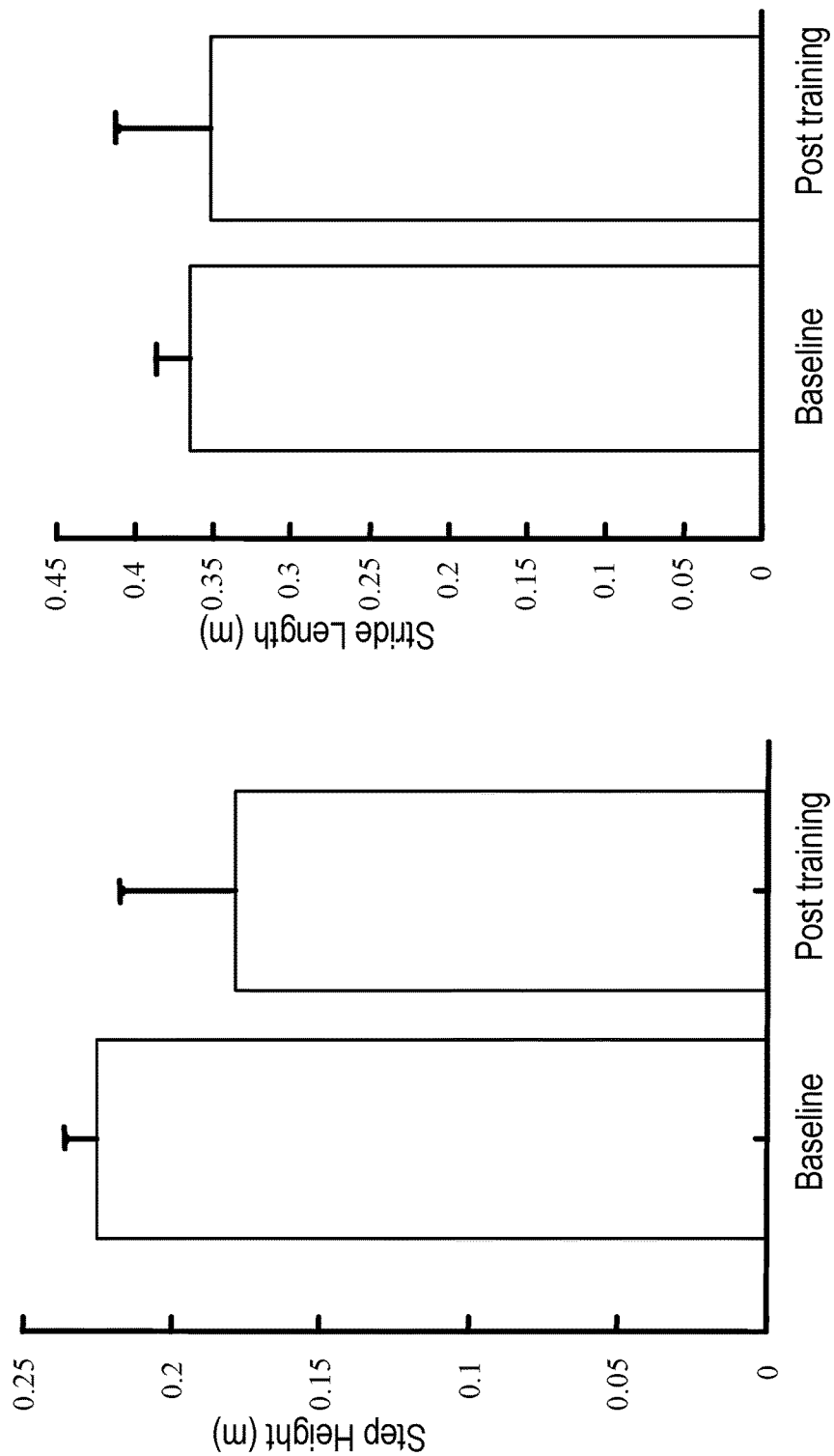
FIG. 5A is a graph showing the average step height of three strides at the baseline (before loading) and post load release for assistance load training.
FIG. 5B is a graph showing the average stride length of three strides at the baseline (before loading) and post load release for assistance load training.

As shown in FIGS. 5A and 5B, both the step height, FIG. 5A, and stride length, FIG. 5B, were reduced after 5 minutes assistance load training on the treadmill, although larger differences were obtained for step height.

FIGS. 5A and 5B are graphs showing the average step height (FIG. 5A) and stride length (FIG. 5B), of three strides at the baseline (before loading) and post load release for assistance load training. A constant assistance load (15N) was applied at the ankle through a cable robot 10 during the swing phase of the gait. The error bar indicates the standard deviation of the step height and stride length of three strides.

Summary of Study 1

Results from this preliminary study indicated that providing targeted resistance to movement during the swing phase of the gait enhanced patient effort, thereby enhancing the efficacy of BWSTT. In addition, following the release of a resistance load, there was a proven aftereffect, including increased step height and stride length, which could improve stepping. Such resistance training effects carry over to overground stepping.

When using the cable driven system 10, the subject was allowed freedom to move his legs in a naturalistic stepping pattern instead of a fixed, standardized trajectory. This approach allowed variability in the kinematics of the stepping, allowed error in the stepping trajectory and more closely mimicked the compliant assistance provided by a physical therapist compared to a fixed-trajectory motion typically provided by robots in locomotor training. Using an AAN/RAT strategy in robotic locomotor training, which mimics the assistance provided by physical therapists, enhanced the efficiency of robotic treadmill training to a greater extent than previously used assistance robotic training paradigms.

In summary, results from this preliminary test indicate that providing targeted resistance to movement enhances the training effects of BWSTT through increased patient effort and by engaging adaptive sensorimotor processes.

Study 2

In this study, evidence was obtained that a subject post stroke adapts to a swing resistance load applied to the paralyzed leg and shows an "after-effect" with the removal of the load. Further, the motor adaptation produced during treadmill training carried over to overground walking with enhanced step length and gait speed following resistance training. In addition, a substantial increase of the overground gait speed was observed following two weeks of repeated exposure to resistance training, suggesting a potential clinical significance with prolonged (weeks) resistance training.

To assess the impact of resistance training on locomotion in individuals post stroke, one subject with chronic stroke (female, 22 months post stroke, left-side paretic weakness with an ankle-foot orthosis) was recruited to participate to this pilot study. A resistant load (10N) was applied to the ankle of the paralyzed leg through a cable robot 10 during the swing phase of gait. Kinematic data from the hip and knee were recorded using two electrogoniometers (Biometrics, Inc, UK) attached at the hip and knee. The length of the lower leg, measured between the ankle and knee axes of rotation and the length of the femur were measured for subsequent calculations of the step height and stride length.

Figure 7A:
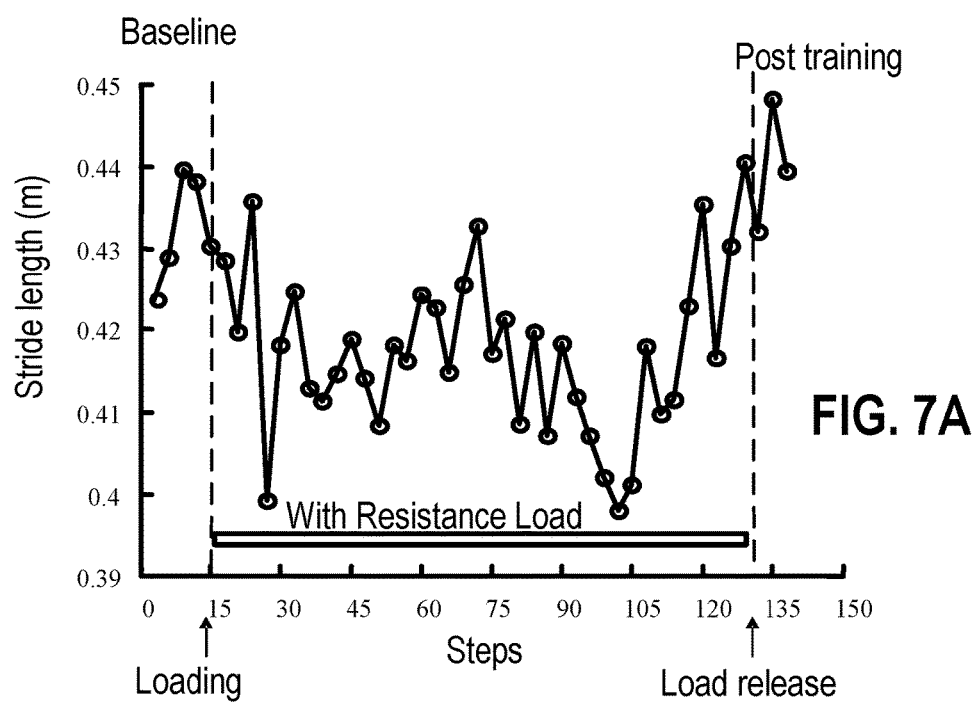
FIG. 7A is a graph plotting a stride-by-stride of step length of a paralyzed leg (from one individual post stroke), showing average values for three steps for a resistive load.
Figure 7B:
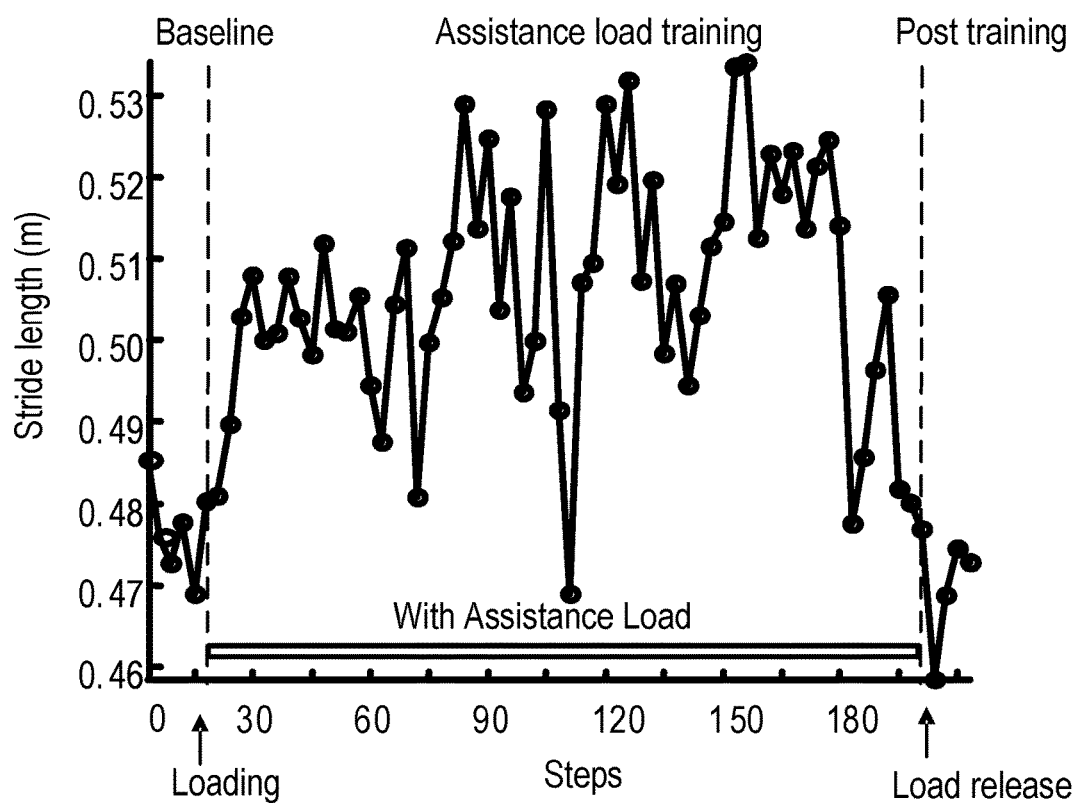
FIG. 7B is a graph plotting a stride-by-stride of step length of a paralyzed leg (from one individual post stroke), showing average values for three steps for an assistive load.

All data were sampled at 1000 Hz using a data acquisition card (National Instruments, Austin, Tex.). An aftereffect consisting of increased step height and stride length was observed following the load release after 10 minutes (a short rest was allowed after first 5 minutes) treadmill training, as shown in FIGS. 7 and 8A and B. Results from pre- and post-resistance load training indicated that both the step height and stride length increased, although a more significant increase was observed for step height (see FIG. 8A, 8B).

FIG. 7 is a stride-by-stride plot of step length of paralyzed leg for one subject following chronic stroke. Each point shown in the figure is the average value of three steps. The subject was fitted into an overhead body weight support system through a harness for safety only and no body weight support was provided. The subject walked on a treadmill with the speed set at 1.7 kPh. A 10N resistance load was applied at the ankle of the paralyzed leg. Resistance load was released following 10 minutes training on the treadmill.

Figure 8B:
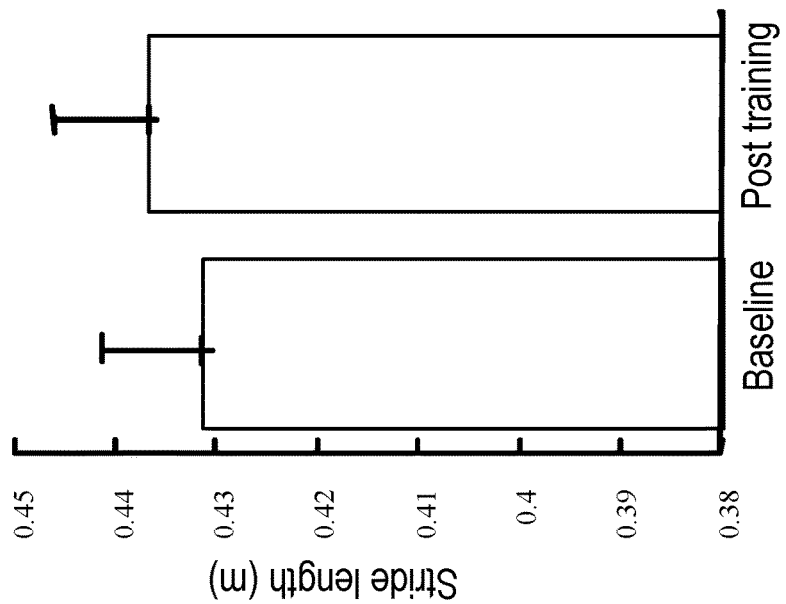
FIG. 8B is a graph showing the average stride length of five strides at the baseline (before loading) and post load release for resistance load training.
Figure 8A:
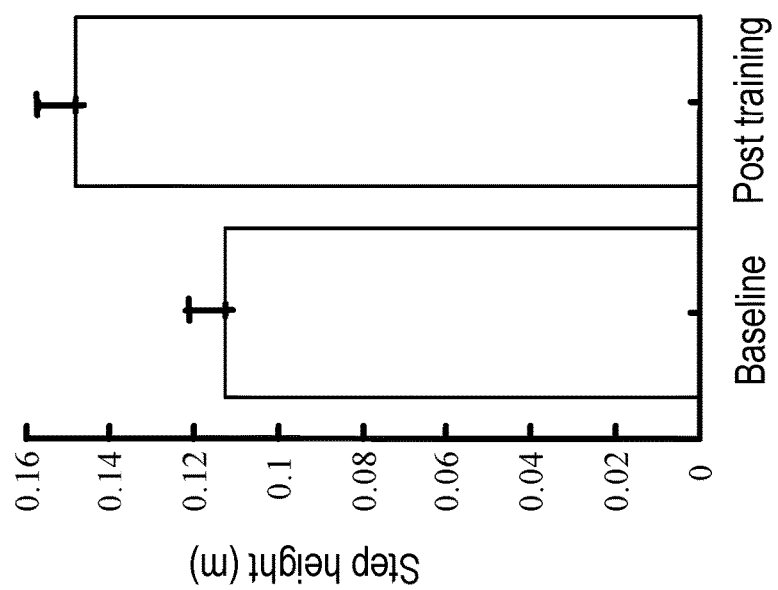
FIG. 8A is a graph showing the average step height of five steps at the baseline (before loading) and post load release for resistance load training.

FIGS. 8A and 8B are graphs illustrating the average step height and stride length of five steps at baseline (before loading) and post load release for resistance load training, A, step height; B stride length. A constant resistance load (10N) was applied at the ankle through a cable driven system during swing phase of the gait. The error bar indicates the standard deviation of the step height and stride length of five steps at the baseline and 10 minutes post training.

In order to test the carryover effect of the motor adaptation obtained during the treadmill training to overground walking, overground gait parameters were measured in the same subject with chronic stroke (female, 37 years old and 22 months post stroke). Overground gait speed and step length of the paralyzed leg (self selected and fast walking) were measured at pre, 10, 20 and 30 minutes post training using a GaitMat II (E.Q. Inc, Chalfont, Pa.). Resistance load (10N) was applied to the ankle of the paralyzed leg during BWSTT through a cable-robot. Following 20 minutes (short rest was allowed after first 10 minutes training) resistance treadmill training, a substantial increase of step length of the paralyzed leg and the gait speed on the overground test was observed for both self selected and fast walking at 10, 20 and 30 minutes post training (see FIGS. 9A and 9B). These results suggest that motor adaptation produced during treadmill training might be transferred to overground locomotion and could be retained at least 30 minutes post training.

Figure 9B:
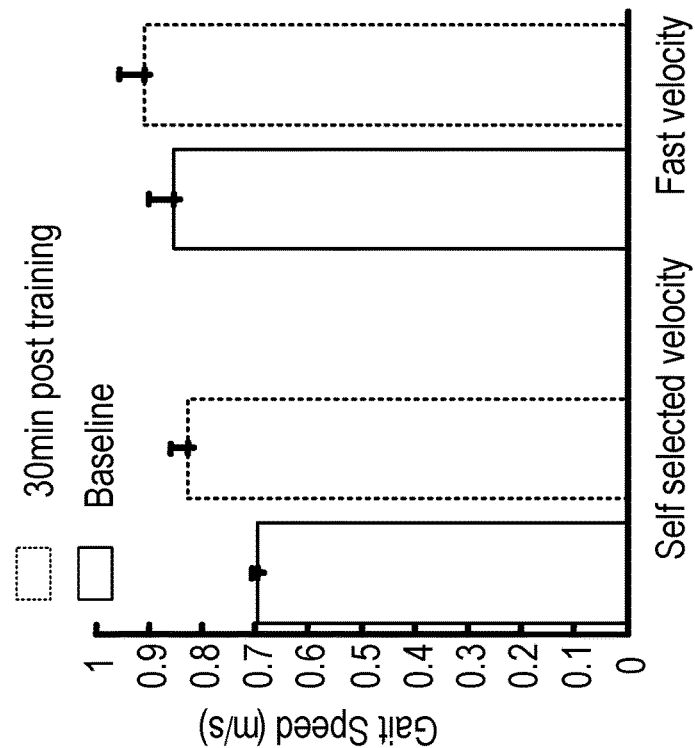
FIG. 9B is a graph showing plots related to overground gait speed prior to and 30 minutes post resistance load training.
Figure 9A:
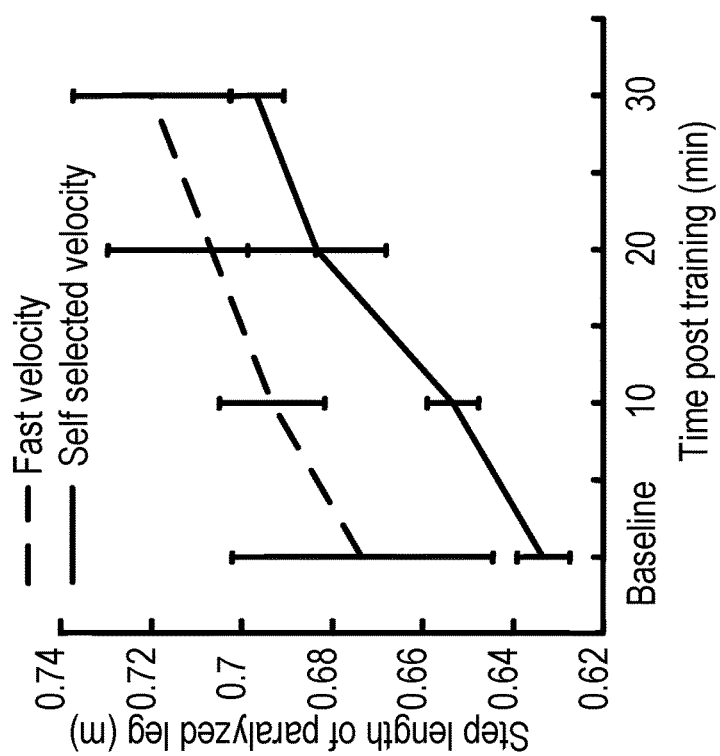
FIG. 9A is a graph showing plots related to the step length of paralyzed leg during overground walking prior to and 10, 20 and 30 minutes post resistance load training.

FIG. 9A is a graph showing plots related to an overground step length of paralyzed leg of one subject post stroke (Female, 37 years old, 22 months post stroke) prior to and 10, 20 and 30 minutes post resistance load training. No body weight was support was actually provided, with an overhead harness used for safety only. The treadmill speed was set at 1.7 kmph. An ankle-foot orthosis and a single point cane were used by the subject during overground walking.

FIG. 9B is a graph showing plots related to gait speed prior to and 30 minutes post training. Three trials were tested for self selected and fast walking with the bar and error bar indicate the average and the standard deviation of gait speed and step length of the paralyzed leg.

In order to test the prolonged retention of the motor adaptation to resistance load, a subject post chronic stroke was recruited to participate in this study. The study consisted of a two weeks (3 visits per week) training protocol and one week follow up test. At each visit, the subject was trained on the treadmill for 20 minutes with a resistance load (10-11N) applied at the ankle of the paralyzed leg through a cable robot. A short rest was allowed after 10 minutes training. The treadmill speed was set at 1.7 kmph and no body weight support was provided, with an overhead harness used for safety only. Overground gait speed was measured at pre, 10, 20 and 30 minutes post training for subject self-selected and fast walking speeds using a GaitMat II (E.Q. Inc, Chalfont, Pa.). Three trials were recorded for each condition.

Results indicated a significant accumulation effect of training on overground gait speed following two weeks of repeated exposure to resistance load training. A substantial increase in gait speed was observed for self selected walking speed (increased from 0.69±0.01 m/s at baseline to 0.89±0.01 m/s post training, and 0.91±0.03 m/s at the follow up) and fast walking (increased from 0.85±0.05 m/s at baseline to 0.96±0.03 m/s post training, and 0.97±0.02 m/s at the follow up) following resistance load training using the cable driven system 10, FIG. 10A.

Figure 6:
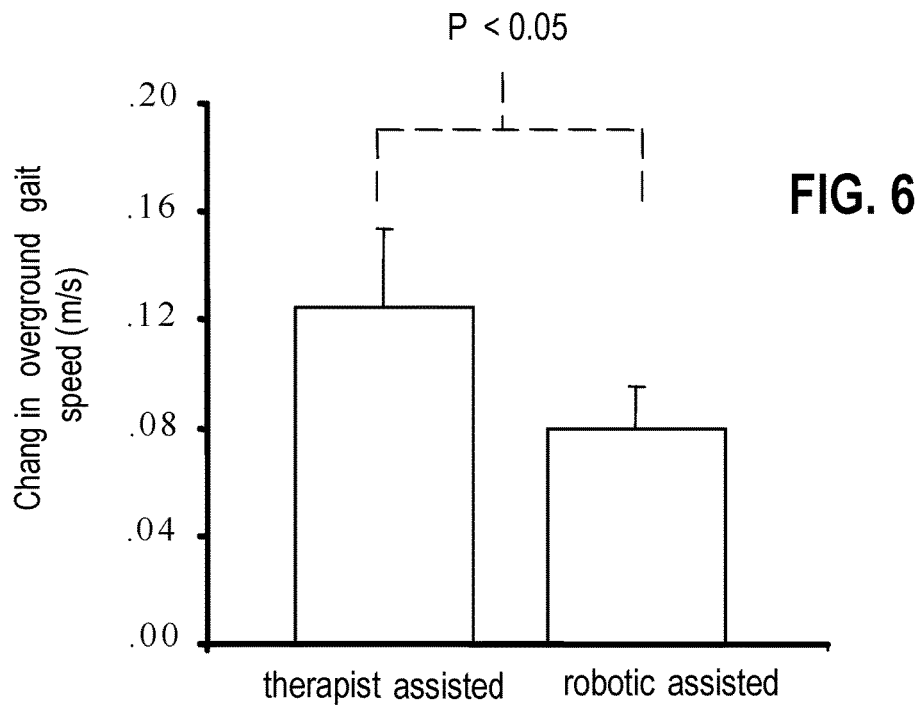
FIG. 6 is a graph illustrating an improvement in overground walking speed after receiving the trajectory fixed robotic-assisted BWSTT.

The improvement of self selected gait speed for this subject following two weeks training was greater than the average values post four weeks BWSTT with assistance provided by a physical therapist (increment 0.20±0.02 vs. 0.13±0.11 m/s) or a robotic system with fixed trajectory (increment 0.20±0.02 vs. 0.07±0.07 m/s), FIG. 6. The improvement of fast walking gait speed for this subject is close to the average values with physical therapist assisted treadmill training (increment 0.11±0.07 vs. 0.13±0.11 m/s) but with less duration of training (6 vs. 12 sessions). In addition, the step length of the paralyzed leg was also increased for self selected and fast walking, indicating a prolonged retention of motor adaptation associated with repeated exposure to resistance load training, FIG. 10B.

Figures 10A, 10B:
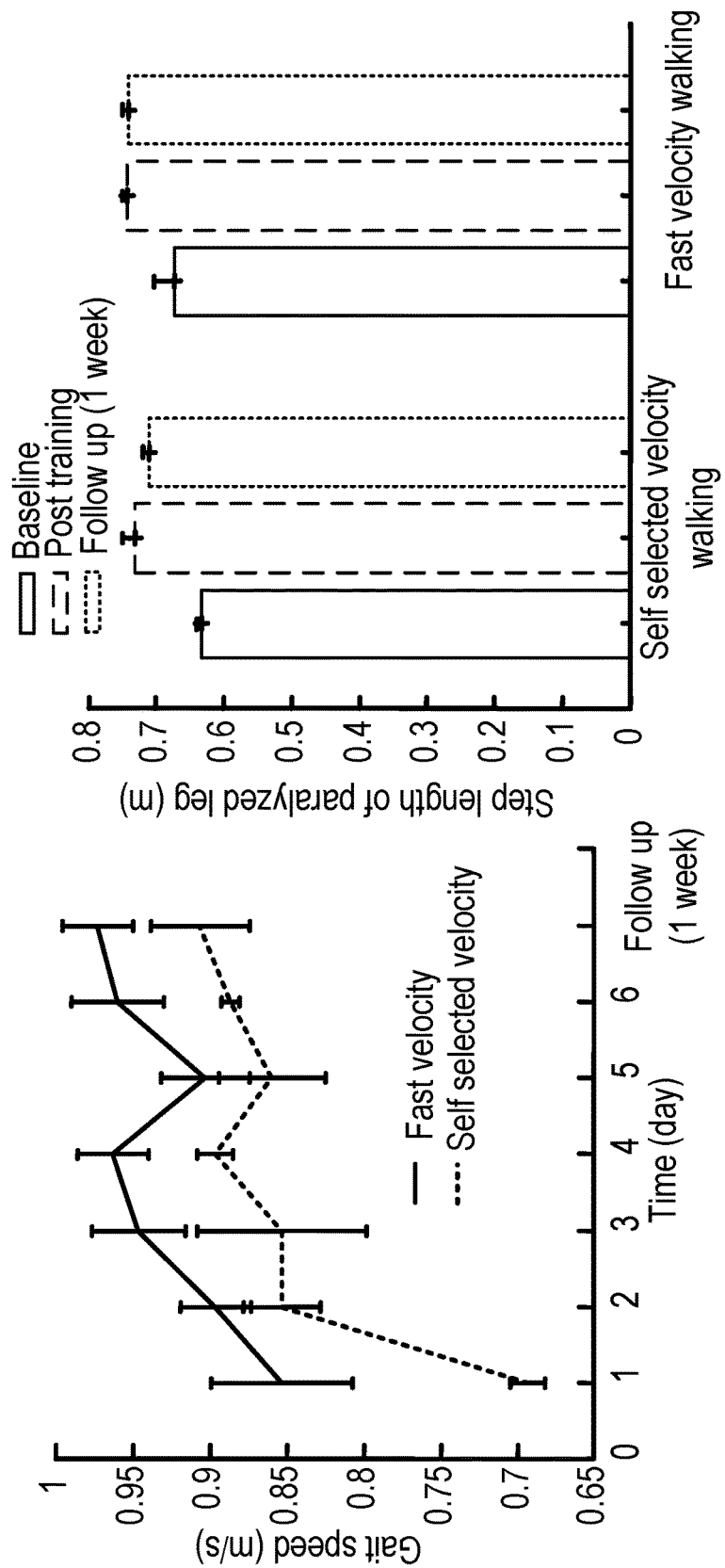
FIG. 10A is a graph showing overground gait speed of an individual post stroke following repeated exposure of resistance load training, with the values being average values of three trials for each condition.
FIG. 10B is a graph showing step length of the paralyzed leg following repeated exposure of resistance load training, with the values being average values of three trials for each condition.

FIGS. 10A and 10B are graphs showing overground speed (FIG. 10A) and step length of the paralyzed leg (FIG. 10B) of one subject post stroke (Female, 37 years old, 22 months post stroke, ankle-foot orthosis was used at the paralyzed leg and a single point cane was used during overground walking) following repeated exposure of resistance load training. The values indicated at the figures are the average values of three trials for each condition.

Summary of Study 2

In summary, results from this study indicate that a swing phase resistance load enhances the training effects of BWSTT through increased patient effort and by engaging adaptive sensorimotor processes. In addition, repeated exposure of the resistance training may produce prolonged retention of the motor adaptation, suggesting a high potential clinical significance of this training paradigm.

Thus, a person suffering from stroke or spinal cord injury can improve the ability to walk by utilizing the inventive system that applies resistance to the person's legs when walking on a treadmill. Resistance of an amount calculated by a computer algorithm in a controller is provided to the legs of a person on the treadmill at a specific phase of the gait cycle in order to maintain a stable stepping. In addition, given exhaustion by the person and locomotor recovery through out the course of training, the load must be varied over time.

The system or systems described herein may be implemented on any form of computer or computers and the components may be implemented as dedicated applications or in client-server architectures, including a web-based architecture, and can include functional programs, codes, and code segments. Any of the computers may comprise a processor, a memory for storing program data and executing it, a permanent storage such as a disk drive, a communications port for handling communications with external devices, and user interface devices, including a display, keyboard, mouse, etc. When software modules are involved, these software modules may be stored as program instructions or computer readable codes executable on the processor on a computer-readable media such as read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. This media can be read by the computer, stored in the memory, and executed by the processor.

All references, including publications, patent applications, and patents, cited herein are hereby incorporated by reference to the same extent as if each reference were individually and specifically indicated to be incorporated by reference and were set forth in its entirety herein.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical".

The use of the terms "a" and "an" and "the" and similar referents in the context of describing the invention (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

Numerous modifications and adaptations will be readily apparent to those skilled in this art without departing from the spirit and scope of the present invention.

TABLE OF ACRONYMS

AAN assistance as needed
ASIA American Spinal Injury Association
BWSTT body weight supported treadmill training
EMG Electromyography
LEMS lower-extremity motor score
RAT resistance as tolerated
SCI spinal cord injury
WISCI walking index for spinal cord injury

TABLE OF REFERENCE CHARACTERS

R Right
L Left
F Front
R Rear
10 cable driven system/robot
12 Person
20 braces or holding element
24 ankle position and/or velocity sensors
40 drive system
42 drive motors
44 cable spools
45 pulleys
46 torque load cells
50 connecting elements
55 treadmill
60 counterbalancing system
61 overhead harness
62 counterbalance pulley
63 counterweight
64 winch
68 group of springs
69 torso harness
70 monitor
80 static motor behavior measurement device
82 motor
84 main axial reaction torque transducer
86 radial arm
88 secondary axial reaction torque transducer
90 foot clamp
100 controller
110 gait phase inputs
120 step kinematic parameter inputs
130 resistance or assistance commands
140 target step kinematic parameters
150 control algorithms
200 method flowchart
210-250 method steps

What is claimed is:

1. A system for providing targeted training to a walking person, comprising:
    a powered backward moving surface for the person to walk on;
    a force-applying element for affixing to a leg of the person;
    a gait phase detector;
    a leg portion position sensor;
    a motor connected to the force-applying element, wherein the motor applies a resistive force to the force applying element; and
    a controller connected to the gait phase detector,
        the leg portion position or leg portion velocity sensor, and
        the motor,
        wherein the controller is configured to
            accept values related to a gait phase from the gait phase detector,
            accept values related to the leg portion position or leg portion velocity from the leg portion position sensor, and
            output a value related to the resistive force of the motor applied to the force-applying element based on the gait phase values and on the leg portion position values, thereby providing the targeted training to the person.

2. The system according to claim 1, wherein the force-applying element comprises:
    a holding element affixed to the leg of the person;
    a front cable attached to a front of the holding element;
    a rear cable attached to a rear of the holding element; and
    one or more spools attached to the motor, wherein the front and rear cables are wound on the one or more spools.

3. The system according to claim 1, further comprising:
    a counterweight system attached to the person for reducing a load on the legs of the person while walking on the powered backward moving surface.

4. The system according to claim 1, further comprising:
    a feedback monitor visible to the person, wherein the feedback monitor displays parameters related to the motor performance of the person.

5. The system according to claim 1, wherein the controller comprises a processor that determines a force applied to the force-applying element according to the following equation:

$$F_r(t)=k_P(e_t-(x_d(t)-x(t)))+k_D(\dot{e}_t-(\dot{x}_d(t)-\dot{x}(t)))$$

where
    t is time;
    $F_r(t)$ is the applied resistive force as a function of time;
    $k_P$ is the position gain (e.g., $k_P$=0.1 N/mm nominal);
    $k_D$ is the velocity gain (e.g., $k_D$=0.05 N/mm/s nominal);
    x(t) is the measured ankle horizontal position during the swing phase;
    $\dot{x}(t)$ is the measured ankle horizontal velocity during the swing phase;
    $x_d(t)$ is the desired ankle horizontal position during the swing phase;
    $\dot{x}_d(t)$ is the desired ankle horizontal velocity during the swing phase;
    $e_t$ is the preset threshold value for the position errors: $e_t$=280 mm nominal; and
    $\dot{e}_t$ is the preset threshold value for the velocity errors: $\dot{e}_t$=25 mm/s nominal.

6. An apparatus for providing targeted training to a person volitionally moving their legs while walking on a powered backward moving surface, comprising:
  a holding element configured to receive a portion of a person's leg;
  a drive system that applies a resistive force to the holding element via a cable attached to the holding element and to the drive system;
  at least one position detector that determines at least one of the horizontal position and horizontal velocity of the person's leg throughout one or more phases of a gait cycle of the person while walking to obtain kinematic information regarding motor performance of the leg;
  a controller that:
    receives the kinematic information from the leg portion position sensor;
    determines a phase of the gait based on the received kinematic information; and
    controls the drive system to, in a swing phase of the gait, apply the resistive force to the leg via the cable to resist a forward swing movement of the leg in an amount that is based on the received kinematic information, thereby providing the targeted training to the person.

7. The apparatus of claim 6, wherein the at least one position detector is one of a plurality of three dimensional detectors and the received kinematic information is ankle horizontal position and horizontal velocity.

8. The apparatus of claim 7, wherein the controller carries out additional steps comprising:
  determining and saving in a memory desired kinematic information comprising a desired measure of horizontal position as a function of time or gait cycle ($x_d(t)$), and a desired measure of horizontal velocity as a function of time or gait cycle ($\dot{x}_d(t)$); and
  utilizing the received kinematic information and the desired kinematic information in determining an amount of the resistive force that is applied to the leg.

9. The apparatus of claim 8, wherein the controller carries out additional steps comprising:
  setting preset threshold values for position errors $e_t$ and velocity errors $\dot{e}_t$ that are used in determining the amount of resistive force that is applied to the leg.

10. The apparatus of claim 9, wherein the resistive force is applied to the leg according to the following equation:

$$F_r(t) = k_P(e_t - (x_d(t) - x(t))) + k_D(\dot{e}_t - (\dot{x}_d(t) - \dot{x}(t)))$$

where
  t is time;
  $F_r(t)$ is the applied resistive force as a function of time;
  $k_P$ is the position gain (e.g., $k_P$=0.1 N/mm nominal);
  $k_D$ is the velocity gain (e.g., $k_D$=0.05 N/mm/s nominal);
  $x(t)$ is the measured ankle horizontal position during the swing phase;
  $\dot{x}(t)$ is the measured ankle horizontal velocity during the swing phase;
  $x_d(t)$ is the desired ankle horizontal position during the swing phase;
  $\dot{x}_d(t)$ is the desired ankle horizontal velocity during the swing phase;
  $e_t$ is the preset threshold value for the position errors: $e_t$=280 mm nominal; and
  $\dot{e}_t$ is the preset threshold value for the velocity errors: $\dot{e}_t$=25 mm/s nominal.

11. The apparatus of claim 6, wherein the drive system comprises a motor and a cable spool, and the motor is arranged to actuate the cable spool.

12. The apparatus of claim 6, wherein the drive system is positioned directly behind the leg during a therapy session.

13. The apparatus of claim 6, further comprising a harness that provides side support to the person.

14. The apparatus of claim 11, wherein the cable applies the resistive force by being wound around the cable spool during actuation of the motor.

15. The apparatus of claim 6, further comprising a reaction torque cell that measures the resistive force.

16. The apparatus of claim 6, wherein the gait phase during which the resistive force is applied is only about 10% of the gait cycle prior to toe off through mid swing.

17. The apparatus of claim 6, wherein the controller performs further steps comprising varying the resistive force across gait cycles to maintain predefined values for step kinematics.

18. The apparatus of claim 17, wherein the predefined values for step kinematics include stride length and step height.

19. The apparatus of claim 6, further comprising ankle position detectors that determine an ankle position of the person, wherein the controller determines of the gait phase by reading information from the ankle position detectors.

20. The apparatus of claim 6, wherein the at least one position detector measures kinematic information of motor performance by measuring EMG data from muscle groups associated with at least one of hip, knee, and ankle muscles.

* * * * *